(12) United States Patent
Loesel et al.

(10) Patent No.: US 7,238,176 B2
(45) Date of Patent: Jul. 3, 2007

(54) METHOD FOR INTRASTROMAL PHOTODISRUPTION OF DOME-SHAPED SURFACES

(75) Inventors: Frieder Loesel, Mannheim (DE); Thomas Sauter, Neckargemuend (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 519 days.

(21) Appl. No.: 10/835,087

(22) Filed: Apr. 29, 2004

(65) Prior Publication Data

US 2005/0245915 A1    Nov. 3, 2005

(51) Int. Cl.
*A61B 18/20*    (2006.01)

(52) U.S. Cl. .................. 606/5; 606/4; 606/10; 128/898

(58) Field of Classification Search .................. 606/4, 606/5, 10–12, 17, 18; 351/205–121; 128/898
See application file for complete search history.

(56) References Cited

U.S. PATENT DOCUMENTS

| | | | |
|---|---|---|---|
| 3,769,963 A | 11/1973 | Goldman et al. | |
| 4,309,998 A | 1/1982 | Aron nee Rosa et al. | |
| 4,391,275 A | 7/1983 | Fankhauser et al. | |
| 4,538,608 A | 9/1985 | L'Esperance, Jr. | |
| 4,633,866 A | 1/1987 | Peyman et al. | |
| 4,665,913 A | 5/1987 | L'Esperance, Jr. | |
| 4,718,418 A | 1/1988 | L'Esperance, Jr. | |
| 4,903,695 A | 2/1990 | Warner et al. | |
| 4,907,586 A | 3/1990 | Bille et al. | |
| 4,941,093 A | 7/1990 | Marshall et al. | |
| 6,110,166 A | 8/2000 | Juhasz | |
| 6,146,375 A * | 11/2000 | Juhasz et al. | 606/6 |
| 6,331,177 B1 * | 12/2001 | Munnerlyn et al. | 606/5 |
| 6,382,797 B1 * | 5/2002 | Bille et al. | 351/212 |
| 6,579,282 B2 * | 6/2003 | Bille et al. | 606/5 |
| 6,610,051 B2 | 8/2003 | Bille | |
| 6,626,895 B2 * | 9/2003 | Frey et al. | 606/10 |
| 6,730,074 B2 * | 5/2004 | Bille et al. | 606/5 |
| 2005/0228366 A1 * | 10/2005 | Kessler et al. | 606/5 |

* cited by examiner

*Primary Examiner*—A. Farah
(74) *Attorney, Agent, or Firm*—Nydegger & Associates

(57) ABSTRACT

A method is disclosed for photodisrupting a surface in the stroma of an eye at a substantially constant distance from the anterior surface of the eye. A frame of reference is established for the eye that includes an axis of rotation. Next, the focal point of a laser beam is positioned in the stroma at a radial distance from the axis. At least one laser pulse is delivered to the stromal tissue at the focal point, photodisrupting the tissue there and creating a photodisruption bubble having a diameter "d". The focal point is then rotated about the axis through an arc length substantially equal to "d" and the photodisruption step is repeated. During rotation, the distance between the focal point and the axis is decreased at a rate substantially equal to the distance "d" per revolution. The method can be used to create a flap for a LASIK type procedure.

18 Claims, 2 Drawing Sheets

METHOD FOR INTRASTROMAL PHOTODISRUPTION OF DOME-SHAPED SURFACES

FIELD OF THE INVENTION

The present invention pertains generally to systems and methods for photodisrupting a pre-selected pattern of intrastromal tissue. More particularly, the present invention pertains to the photodisruption of a substantially dome-shaped layer of corneal tissue using a femtosecond laser. The present invention is particularly, but not exclusively, useful for creating a flap that can be used as part of a LASIK type procedure to correct the refractive properties of the cornea.

BACKGROUND OF THE INVENTION

In a typical Laser In-Situ Keratomeleusis (LASIK) procedure, a microkeratome is used to incise the cornea of a patient and create a flap. The flap is then lifted to expose a bed of stromal tissue which is subsequently ablated using an Excimer laser. The use of a mechanical device, such as a microkeratome, to create a flap has several disadvantages. For example, the creation of a suitable flap with the microkeratome relies heavily on the skill and eye-hand coordination of the surgeon. In such operations, complications can result if the flap is cut improperly or is completely severed from the cornea. In addition, the use of a microkeratome often produces an irregular incision. As a consequence, the bed of tissue that is exposed when the flap is lifted often contains surface irregularities that can create wrinkles when the flap is replaced. These wrinkles can produce undesirable vision deficiencies. As an additional drawback, the incision produced by a microkeratome is typically not substantially dome-shaped or parallel to the anterior surface of the cornea. Because the bed of exposed tissue is not parallel to the anterior surface of the cornea, the laser ablation step can be relatively complicated, is often difficult to control, and can result in an ablation that is somewhat uneven relative to the natural curvature of the cornea. This is especially troublesome when the ablation of a uniform thickness of tissue is prescribed to correct an optical deficiency. For example, the ablation of a uniform volume of tissue is typically prescribed to treat myopia (i.e. nearsightedness), which is a widely occurring condition among the adult population.

As an alternative to using a microkeratome, a laser can be used to create a flap for a LASIK type procedure. For example, a train of laser pulses having pulse durations in the femtosecond range, can be directed to a focal point at a predetermined location within a patient's cornea to photodisrupt tissue at the focal point with precision and accuracy. The photodisruption of tissue by femtosecond lasers results from a process called laser induced optical breakdown (LIOB). Specifically, in the LIOB process, optical breakdown occurs in the laser focus due to the extremely high local electrical field strength that is generated. This field exceeds the binding energy of the valence electrons to their atoms, resulting in the generation of a microplasma, gas bubbles and shockwaves.

An example of a procedure that uses a pulsed laser beam focused at a predetermined, subsurface location within a patient's cornea is disclosed in U.S. Pat. No. 4,907,586, which issued to Bille et al. for an invention entitled "Method for Reshaping the Eye". In greater detail, the above-cited Bille patent discloses the use of a pulsed laser beam for subsurface photodisruption of intrastromal tissue. Unlike the Excimer laser used after flap creation in the conventional LASIK procedure, the pulsed laser beam, as disclosed by Bille, penetrates corneal tissue and can be focused at a point below the surface of the cornea to photodisrupt stromal tissue at the focal point.

The ability to reach a subsurface location without necessarily providing a physical pathway allows for volumes of stromal tissue to be photodisrupted having complicated shapes while minimizing the amount of total tissue disrupted. To create these shapes, the laser beam is first directed to a focal point (using suitable optics to include a cutting lens) at a target location corresponding to a point on the desired volume to be photodisrupted. After at least one pulse is delivered to the focal point to ablate the tissue there, the focal point is moved (i.e. scanned) to another point in the prescribed volume. At the new location, at least one pulse is delivered and the process of scanning and ablating is continued until the entire prescribed volume of tissue is photodisrupted.

From the above discussion, it is apparent that the accuracy, agility and speed of the scanning sub-system can have a large impact on the overall performance of the surgical system. Stated another way, the scanning system is responsible for accurately and very quickly moving the focal point from one prescribed location to another. This demand on the scanning system can be especially acute when scanning is required in all three dimensions (i.e. a movement from one location to the next requires a simultaneous movement in an "x", "y" and "z" direction). In an effort to simplify this requirement, one technique has been developed which requires the scanning system to scan in only two (rather than three) mutually orthogonal directions. For this technique, the cornea is first applanated to obviate the need for scanning movements in the z direction. This is done by conforming the anterior surface of the cornea against a substantially flat applanating lens. Next, a planar volume of subsurface tissue parallel to the applanating lens is ablated. With the use of a specialized cutting lens having no field curvature, the planar volume can be ablated with only two-dimensional scanning (i.e. scan movements normal to the applanating lens surface are not required). However, as developed further below, this technique can result in several rather severe and undesirable consequences.

Although scanning is simplified, flattening of the cornea can have undesirable consequences. For example, flattening of the cornea can result in severe discomfort for the patient. Moreover, flattening of the cornea can increase the intraocular pressure to dangerously high levels. Lastly, but perhaps of equal importance, severe flattening of the cornea can distort the three-dimensional architecture of the corneal lamellae. The result of this distortion is that an incision that is made while the cornea is severely flattened, changes shape in an unpredictable way when the cornea is relaxed.

For the case where scanning the three mutually orthogonal directions is contemplated, a number of factors can impact system performance. Among these factors involves the scan distance that the focal point must be moved from one ablation point to the next. As this scan distance increases, larger scan movements are required. As recognized by the present invention, scan accuracy is typically proportional to scan distance. Accordingly, by reducing the scan distance, scan accuracy can be improved. In addition, relatively large scan movements often result in increased wear on the scanner system components. This wear can decrease the life of the scanner system. Lastly, short scan movements can be executed faster than large scan movements. Thus, it is desirable to use an ablation scan pattern which minimizes scan movements between consecutively ablated spots to thereby quicken the procedure. In somewhat simpler terms, for a given scan response time, shorter scan movements can accommodate the use of a faster laser pulse repetition rate and result in a shorter overall procedure time.

In light of the above, it is an object of the present invention to provide systems and methods suitable for the purposes of photodisrupting subsurface ablations having relatively complex shapes such as a substantially dome-shaped layer of stromal tissue. It is another object of the present invention to provide methods for creating a flap that can be used as part of a LASIK type procedure, and particularly, a flap which exposes a surface for ablation that is substantially parallel to the natural, anterior surface of cornea. It is yet another object of the present invention to provide a method for photodisrupting a preselected volume of tissue using a series of relatively small scan movements. Yet another object of the present invention is to provide a method for photodisrupting stromal tissue at a plurality of subsurface focal points which is easy to use, relatively simple to implement, and comparatively cost effective.

SUMMARY OF THE INVENTION

The present invention is directed to systems and methods for photodisrupting a pre-selected volume of corneal tissue. In one application of the invention, a substantially dome-shaped layer of subsurface stromal tissue is ablated using a focused laser beam. With this method, a corneal flap can be created and used as part of a LASIK type procedure to correct the refractive properties of the cornea.

In one aspect of the invention, a method is disclosed which begins by identifying the "x", "y" and "z" coordinates for each of a plurality of locations within the cornea. Specifically, coordinates are identified such that photodisruption at each location results in a photodisruption of the pre-selected volume. Typically, the coordinates are identified by first creating a two-dimensional, planar spot pattern and thereafter transforming the planar spot pattern into a three-dimensional, non-planar pattern. For example, to identify the coordinates for photodisruption of a dome-shaped layer, a planar spot pattern such as a two dimensional spiral is first created (e.g. in x-y space). Next, a "z" component (wherein a "z" direction is orthogonal to both "x" and "y" directions) is added to each spot in the planar pattern to transform the planar pattern into the three-dimensional set of coordinates.

Once the coordinates of locations for photodisruption within the cornea have been identified, the next step is to generate a focused laser beam and scan the focal point of the beam from location to location within the cornea. For this purpose, a laser system having a laser source, laser scanner and one or more optical elements is provided. In one setup, the laser system can include, in order, a laser source, a laser scanner for scanning in three dimensions, a plurality of lenses arranged as a telescope, a mirror and a cutting lens. In some implementations, a contact lens is used to stabilize the cornea relative to the laser source and conform the anterior surface of the eye to a pre-selected radius of curvature, R. Typically, this radius of curvature, R, substantially corresponds to the natural curvature of the cornea's anterior surface and is in a range of between approximately 7.5 mm and approximately 11.0 mm. In most cases, a radius of curvature, R, of approximately 8.8 mm is used. With the above-described cooperation of structure, a laser beam can be generated and sequentially directed through the scanning system, optical element and contact lens to a focal point at one of the pre-identified locations within the cornea.

To photodisrupt corneal tissue at each location, a sequence of laser canner positions is calculated. Input data for calculating the scanner positions can include the optical characteristics of the optical element (i.e. the telescope, mirror and cutting lens for the arrangement described above), and, if used, the contact lens. Specifically, this input data can include the optical characteristic for a plurality of paths through the optical element and contact lens. The calculated sequence of laser scanner positions is then used to move the focal point of the laser beam from location to location to photodisrupt the pre-selected volume of tissue.

In another aspect of the invention, a method is provided for photodisrupting a surface in the stroma of an eye at a substantially constant distance from the anterior surface of the eye. For this method, a frame of reference is established for the eye that includes an axis of rotation (e.g. the optical axis of the eye). Next, the focal point of a laser beam is positioned in the stroma at a radial distance "r" from the axis of rotation. At least one laser pulse is delivered to the stromal tissue at the focal point, photodisrupting the tissue there and creating a photodisruption bubble having a diameter "d". After photodisruption at the first location, the focal point is then rotated about the axis of rotation through an angle "θ" and through an arc length substantially equal to "d". The photodisruption step is then repeated. As this sequence of photodisruption continues, the distance between the focal point and the axis of rotation is gradually decreased at a rate that is substantially equal to the distance "d" per revolution (i.e. $\Delta r/rev = d/rev$). In addition, the "z" component is controlled to photodisrupt a surface that is at a substantially constant distance from the anterior surface of the eye. Typically, both the angular rate of rotation "w" and the radial velocity of the focal point is increased as the focal point moves closer to the rotation axis.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
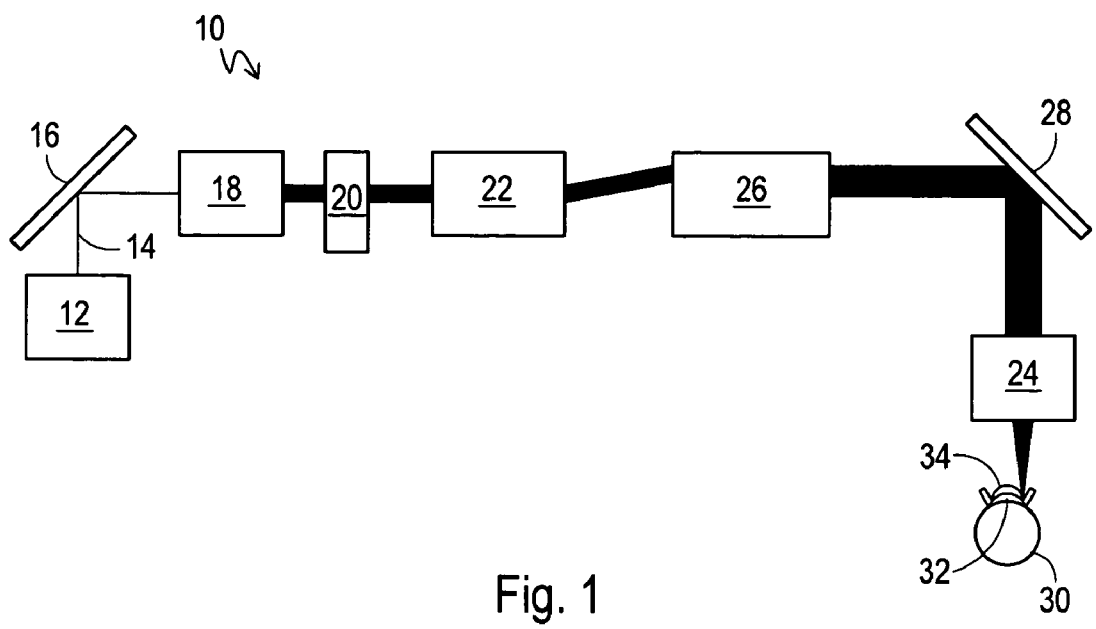
FIG. 1 is a schematic view showing the primary optical components of a system for photodisrupting a pre-selected volume of corneal tissue.

Referring to FIG. 1, an ophthalmic laser system for intrastromal subsurface photodisruption (by the effect of laser induced optical breakdown (LIOB)) is shown and generally designated 10. As shown in FIG. 1, the system 10 includes a laser source 12 for producing a pulsed laser beam and directing the laser beam along a first beam path 14. A typical embodiment of the laser source 12 includes an all solid-state fs-laser with a pulse duration of 1 fs to about 100 ps, an operating wavelength in the near infrared and repetition rate in the range of 1-100 kHz.

Continuing with reference to FIG. 1, it can be seen that the laser beam generated at the laser source 12 is directed along the beam path 14 where it is reflected using a forty-five degree mirror 16. From the mirror 16, the beam is directed into a plurality of lenses that are arranged as a Galilei telescope 18. In the telescope 18, the laser beam is expanded by a factor of two (in some setups the beam is expanded by a factor of three) and forwarded to the master shutter 20. The master shutter 20 acts as a safety element. After passing the shutter 20, the beam enters a scanning unit 22.

The scanning unit 22 typically includes a fixed plano-convex lens that is distanced along the optical beam path from a moveable plano-concave lens to provide z-position control (z-axis shown in FIG. 2) of the laser beam focal point. A voice coil (not shown) can be used to move the piano-concave lens. In addition, the scanning unit 22 can include an x-y scanner having galvanometer mirrors.

A more thorough description of a suitable scanning unit 22 and its operation is provided in co-pending, co-owned U.S. patent application Ser. No. 10/821,402, titled "Beam Steering System for Corneal Laser Surgery" and is hereby incorporated by reference in its entirety herein.

For the system 10, control signals are routed to a unit processor (not shown) where they are processed by, for example, a real-time operating system and evaluated by adequate hardware tools. If an error in laser output or positioning occurs during a procedure or calibration, the master shutter 20 is activated to block the beam to prevent any detrimental radiation from reaching the patient's eye.

Continuing with FIG. 1, it can be seen that after leaving the scanning unit 22, the beam is relayed to a cutting lens 24. Specifically, as shown, the beam passes first through a plurality of lenses 26 that are arranged as a telescope and is then reflected by a forty-five degree dichroic mirror 28. The dichroic mirror 28 permits the observation of the patient's eye 30 via a microscope (not shown) through the mirror 28 and cutting lens 24.

Figure 2:
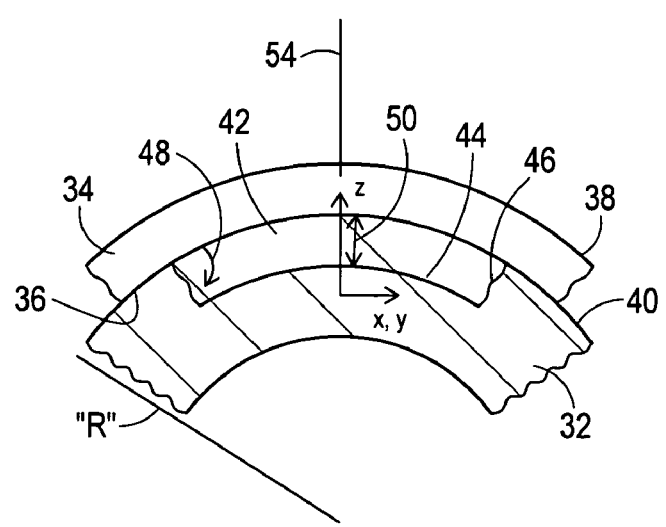
FIG. 2 is an enlarged cross-sectional view of a cornea that has been incised to create a flap for a LASIK type procedure.

Cross-referencing FIG. 1 with FIG. 2, it can be seen that the system 10 includes a contact lens 34, which is typically made of transparent PMMA, and is formed with a posterior surface 36 and an anterior surface 38 to stabilize the cornea 32 relative to the cutting lens 24. As best seen in FIG. 2, the posterior surface 36 of the contact lens 34 is formed with a substantially constant, pre-selected, radius of curvature, R. Moreover, as shown, the contact lens 34 is positioned in contact with the cornea 32 to conform the anterior surface 40 of the cornea 32 with the posterior surface 36 of the contact lens 34. Typically, the radius of curvature, R, is in a range of between approximately 7.5 mm and approximately 11.0 mm. In most cases, a radius of curvature, R, of approximately 8.8 mm (which is close to the natural curvature of the cornea's exterior surface) is used. With the contact lens 34, a severe flattening of the cornea 32 is avoided.

The fixation and alignment of the patient's eye 30 is accomplished using the contact lens 34 and a spacer cone (not shown). For this purpose, the contact lens 34 is applied to and held against the eye 30 using a suction cone (not shown) that is attached to the contact lens 34. Once centered on the eye 30, the suction cone is fixed by applying a vacuum. Next, the spacer cone is placed between the beam exit of the cutting lens 24 and the spacer cone. Using a motorized patient chair, the eye 30 and suction cone are moved towards the spacer cone. The connection between the suction cone and the spacer cone is self-centering to maintain a proper x-y alignment. Furthermore, the setup provides the correct "z" distance between the patient's eye 30 and the cutting lens 24. A pressure sensor (not shown) is used to measure the pressure on the eye 30 when the contact between the spacer cone and the suction cone is established. A more thorough description of the fixation and alignment system and its operation is provided in co-pending, co-owned U.S. patent application Ser. No. 10/790,625, titled "System and Method for Positioning a Patient for Laser Surgery" and is hereby incorporated by reference in its entirety herein.

FIG. 2 shows a cornea 32 that has been partially dissected (i.e. incised) to create a flap 42 for a LASIK type procedure. As shown, the incision to create the flap 42 includes a substantially dome-shaped flap bed cut 44 and a rim cut 46 that partially surrounds the bed cut 44, leaving a "hinge" to allow the flap 42 to be lifted and thereafter replaced. The rim cut 46 is made at a rim angle 48 to the anterior surface 40 of the cornea 32 which, as shown, is typically slightly less than ninety degrees. The flap bed cut 44 is typically made within the stromal portion of the cornea 32 and defines a flap thickness 50. An exemplary flap 42 for a LASIK type procedure can have a flap thickness 50 which is generally in the range of about 140-200 μm and a flap bed diameter in the range of about 5.5-10.0 mm. As alluded to above, for some applications, it is preferable that the flap bed cut 44 is created parallel to the anterior surface 40 of the cornea 32, and thus, for the setup shown, it is preferable that the flap bed cut 44 follow the contour of the posterior surface 36 of the contact lens 34.

Figure 3:
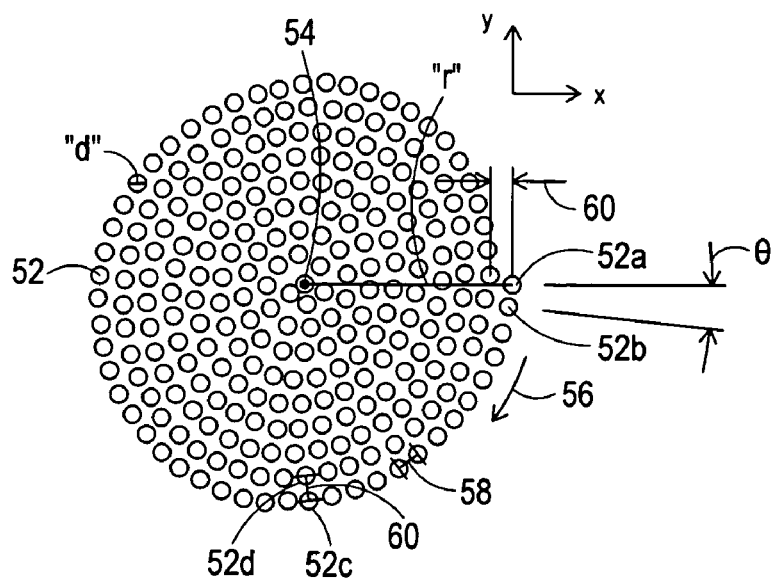
FIG. 3 is a schematic diagram showing a suitable photo-disruption bubble pattern to create a flap for a LASIK type procedure.

In one implementation of the system 10, the flap bed cut 44 is created by first identifying a plurality of focal point locations within the cornea 32. Specifically, focal point locations are identified such that photodisruption at each location results in a photodisruption of the pre-selected volume. FIG. 3 illustrates a pattern of bubbles 52 which result from the photodisruption of a plurality of focal point locations. The bubbles 52 shown in FIG. 3 combine to create a dome-shaped incision (i.e. the flap bed cut 44 shown in FIG. 2). Typically, the set of focal point locations is identified by first creating a two-dimensional, planar spot pattern. For the pattern of bubbles 52 shown in FIG. 3, the initial planar spot pattern is a spiral shaped arrangement. In one implementation, the spiral of focal spots can be deduced from an Archimedes spiral combined with an I-parameterization. Specifically, an Archimedes spiral can be deduced from a point moving with constant angular velocity as well as the constant radial velocity. As a consequence, the arms of the spiral will have a constant distance. Typically, an equal spot spacing is desired radially as well as on the path of the spiral. This implies that the angular velocity and radial velocity are not constant. Instead, both velocities have to be higher in the center of the spiral than in the periphery (i.e. I-parameterization).

Figure 4:
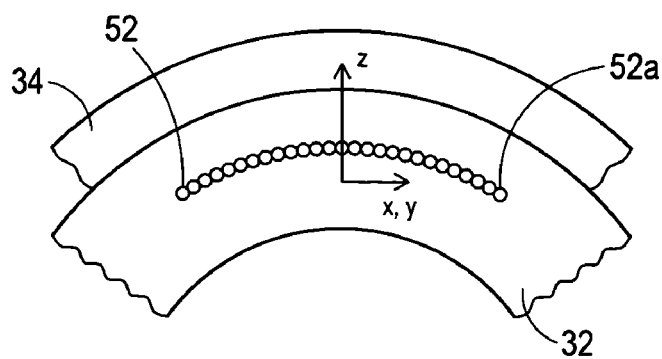
FIG. 4 is an enlarged cross-sectional view of a cornea as in FIG. 2 showing a suitable photodisruption bubble pattern to create a flap for a LASIK type procedure.

Next, the planar spot pattern is transformed into a three-dimensional, non-planar spot pattern. Comparing FIG. 3 with FIG. 4, it can be seen that a "z" component is added to each spot in the planar pattern to transform the planar pattern into the three-dimensional set of coordinates. This latter set of coordinates defines the locations that are individually photodisrupted to create the dome-shaped photodisruption volume.

Once the set of coordinates has been identified, the system 10 shown in FIG. 1 is then used to generate a focused laser beam and scan the focal point of the beam from location to location within the cornea 32. For this purpose, a sequence of laser scanner positions is calculated to move the focal point along a path within the cornea 32 to sequentially photodisrupt corneal tissue at each location corresponding to one of the identified coordinates. For the system 10, each laser scanner position in the sequence includes a tilt angle for each of the galvanometer mirrors and a distance between the fixed plano-convex lens and the moveable plano-concave lens.

Included as input data in the calculation of each laser scanner position is the optical characteristic of one or more of the optical components between the scanning unit 22 and the cornea 32. For the system 10 shown in FIG. 1, these optical components include the lenses 26, mirror 28, cutting lens 24 and contact lens 34. For example, refraction at the interface between the contact lens 34 and cornea 32 as well as all other refractive interfaces between the scanning unit 22 and the contact lens 34 can be used as inputs to the calculation.

Moreover, input data for the calculation can include the optical characteristics for a plurality of paths through the optical components between the scanning unit 22 and the cornea 32. Once calculated, the sequence of laser scanner positions is used to move the focal point of the laser beam from location to location within the cornea 32 to photodisrupt the pre-selected volume of tissue.

In one implementation of the system 10, photodisruption of a dome-shaped volume is conducted in a particular manner. Specifically, in this implementation and as shown in FIG. 2, a frame of reference is established for the cornea 32 that includes an axis of rotation 54. For example, the axis of rotation 54 can be coincident with the optical axis of the eye 30, the visual axis of the eye 30 or can be selected arbitrarily. Next, the focal point of a laser beam is positioned in the stroma at a radial distance "r" from the axis of rotation 54. Referring now to FIG. 3, at least one laser pulse is delivered to the stromal tissue at the focal point, photodisrupting tissue and creating a photodisruption bubble 52a having a diameter "d". After photodisruption at the first location, the focal point is then rotated about the axis of rotation 54 through an angle "θ" in the direction of arrow 56. This moves the focal point through an arc length 58 that is substantially equal to "d." The photodisruption step is then repeated (e.g. photodisruption bubble 52b). During this rotation, the distance between the focal point and the axis of rotation 54 is decreased at a rate substantially equal to the distance "d" per revolution (d/rev). Thus, as shown in FIG. 3, after each complete rotation, the radius "r" is decreased by the distance "d." This is the same everywhere. For example, bubble 52c is radially separated from bubble 52d by a distance 60 of approximately "d". Also during rotation, the focal point is moved toward the anterior surface 40 of the cornea 32 (see FIG. 2) to create the dome-shaped contour. Focal point movement in a direction toward the anterior surface 40 of the cornea 32 can occur as little as once per revolution, with each focal point movement, or with some other pre-selected rate. As illustrated by arrow 56, the focal point is moved from the periphery of the dome-shaped surface to the center of the dome shaped surface. The result is a photodisrupted surface that is created at a substantially constant distance from the anterior surface 40 of the cornea 32.

While the particular Systems and Methods for Intrastromal Photodisruption Dome-Shaped Surfaces as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A method for photodisrupting a surface in the stroma of an eye, at a substantially constant distance from the anterior surface of the eye, the method comprising the steps of:
    establishing a frame of reference for the eye, wherein the frame of reference includes an axis of rotation;
    positioning the focal point of a laser beam in the stroma at a radial distance from the axis of rotation;
    photodisrupting tissue at the focal point to create a bubble having a diameter "d";
    rotating the focal point about the axis of rotation through an arc length substantially equal to "d" to repeat the photodisrupting step; and
    decreasing the distance of the focal point from the axis of rotation, at a rate substantially equal to the distance "d" per revolution, during the rotating step.

2. A method as recited in claim 1 further comprising the step of moving the focal point in a direction substantially parallel to the axis during the rotating step.

3. A method as recited in claim 2 wherein the rotating, decreasing and moving steps are accomplished using a laser scanner configured to contemporaneously scan a focal point in three mutually orthogonal directions.

4. A method as recited in claim 2 wherein the focal point is moved toward the anterior surface of the eye during the moving step.

5. A method as recited in claim 1 further comprising the steps of:
    providing a contact lens formed with an anterior surface and a posterior surface, with the posterior surface having a radius of curvature, R; and
    engaging the cornea with the contact lens to conform the anterior surface thereof with the posterior surface of the contact lens.

6. A method as recited in claim 5 wherein the radius of curvature, R, of the posterior surface of the contact lens is in a range of between approximately 7.5 mm and approximately 11.0 mm.

7. A method for moving a laser beam focal point within the cornea of an eye to photodisrupt a pre-selected volume of corneal tissue, wherein the cornea has an anterior surface, the method comprising the steps of:
    providing a contact lens formed with an anterior surface and a posterior surface with the posterior surface having a radius of curvature, R;
    engaging the contact lens with the cornea to conform the anterior surface thereof with the posterior surface of the contact lens;
    identifying a set of coordinates for each of a plurality of locations within the cornea wherein a photodisruption at each location results in a photodisruption of the pre-selected volume
    providing a laser system having a laser source, laser scanner and an optical element with a cutting lens;
    generating a laser beam and sequentially directing the laser beam through the scanning system, the optical element and the contact lens to a focal point at one of the locations within the cornea;
    calculating a sequence of laser scanner positions from input data for moving the focal point along a path within the cornea to photodisrupt corneal tissue at each of the identified coordinates, the input data including optical characteristics of the optical element for a plurality of beam paths therethrough; and
    using the sequence of laser scanner positions to move the focal point of the laser beam along the path and photodisrupt the volume of tissue.

8. A method as recited in claim 7 wherein the pre-selected volume of corneal tissue is a substantially dome-shaped layer.

9. A method as recited in claim 7 wherein the optical element comprises a plurality of lenses arranged as a telescope.

10. A method as recited in claim 7 wherein the optical element comprises a mirror and a plurality of lenses arranged as a telescope.

11. A method as recited in claim 7 wherein the identifying step comprises the steps of:
creating a planar pattern of locations; and
transforming the planar pattern into a non-planar pattern to obtain the identified coordinates.

12. A method as recited in claim 11 wherein the planar pattern of locations is formed as a spiral.

13. A method as recited in claim 11 wherein the curvature, R, of the contact lens is used as an input to the transforming step.

14. A system for photodisrupting a surface in the stroma of an eye, at a substantially constant distance from the anterior surface of the eye, the eye establishing a frame of reference which includes an axis of rotation, the system comprising:
a contact lens formed with an anterior surface and a posterior surface, with the posterior surface having a radius of curvature, R, the contact lens for engaging the cornea to conform the anterior surface thereof with the posterior surface of the contact lens;
a means for positioning the focal point of a laser beam in the stroma at a radial distance from the axis of rotation;
a means for photodisrupting tissue at the focal point to create a bubble having a diameter "d"; and
a means for rotating the focal point about the axis of rotation through an arc length substantially equal to "d" while decreasing the distance of the focal point from the axis of rotation, at a rate substantially equal to the distance "d" per revolution.

15. A system as recited in claim 14 further comprising a means for moving the focal point in a direction substantially parallel to the axis during rotation of the focal point about the axis of rotation.

16. A system as recited in claim 15 wherein the rotating means and the moving means comprise a laser scanner configured to scan a focal point in three mutually orthogonal directions.

17. A system as recited in claim 14 wherein the moving means moves the focal point toward the anterior surface of the eye.

18. A system as recited in claim 14 wherein the radius of curvature, R, of the posterior surface of the contact lens is in a range of between approximately 7.5 mm and approximately 11.0 mm.

* * * * *